United States Patent [19]

Kranbuehl et al.

[11] Patent Number: 5,119,022
[45] Date of Patent: Jun. 2, 1992

[54] TANK CIRCUIT SENSOR FOR MONITORING RESIN GRAPHITE COMPOSITE FIBER DENSITIES

[75] Inventors: David E. Kranbuehl, Williamsburg; Robert L. Fox, Hayes, both of Va.

[73] Assignee: Center for Innovative Technology, Herndon, Va.

[21] Appl. No.: 710,516

[22] Filed: Jun. 3, 1991

[51] Int. Cl.⁵ .................... G01N 27/72; G01R 33/12; G01R 27/00
[52] U.S. Cl. .................... 324/234; 324/236; 324/655
[58] Field of Search ............... 324/652, 655, 635, 234, 324/236, 229; 264/40.1; 526/60, 59

[56] References Cited

U.S. PATENT DOCUMENTS

| | | | |
|---|---|---|---|
| 3,473,111 | 10/1969 | Leersnijder et al. | 324/236 |
| 3,477,018 | 11/1969 | Richardson et al. | 324/236 |
| 3,586,966 | 6/1971 | Haisty | 324/236 |
| 4,267,519 | 6/1986 | Zatsepin et al. | 324/235 |
| 4,639,669 | 1/1987 | Howard et al. | 324/229 |
| 4,678,994 | 7/1987 | Davies | 324/236 |
| 4,763,071 | 8/1988 | McGee et al. | 324/235 |
| 4,891,591 | 1/1990 | Johnston et al. | 324/236 |

Primary Examiner—Kenneth A. Wieder
Assistant Examiner—Maura K. Regan
Attorney, Agent, or Firm—Whitham & Marhoefer

[57] ABSTRACT

An L-C circuit (tank circuit) is located in close proximity to polymer impregnated composite material layers during the fabrication process. Applicant has determined that the resonant frequency of the tank circuit and the shape of the frequency absorption curve vary as a function of the fiber density of polymer impregnated composite material. The frequency of the input to the tank circuit is periodically swept through a range of frequencies, and the tank circuit impedance is measured to determine the resonant frequency and shape of the frequency absorption curve.

1 Claim, 2 Drawing Sheets

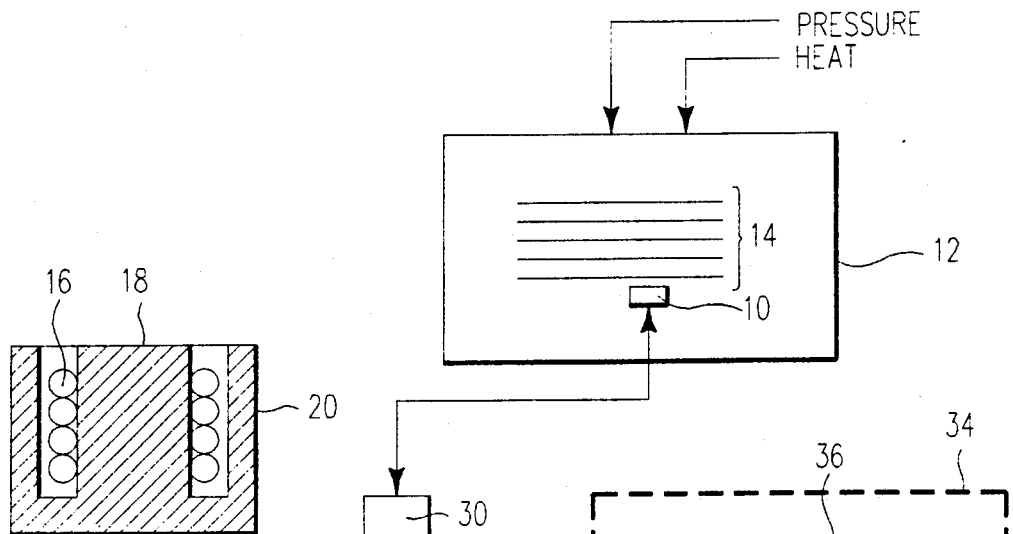
FIG. 1
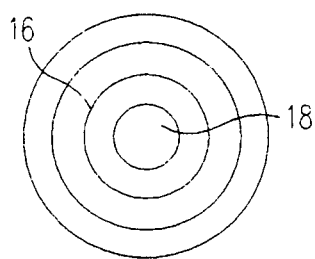
FIG. 2
FIG. 3
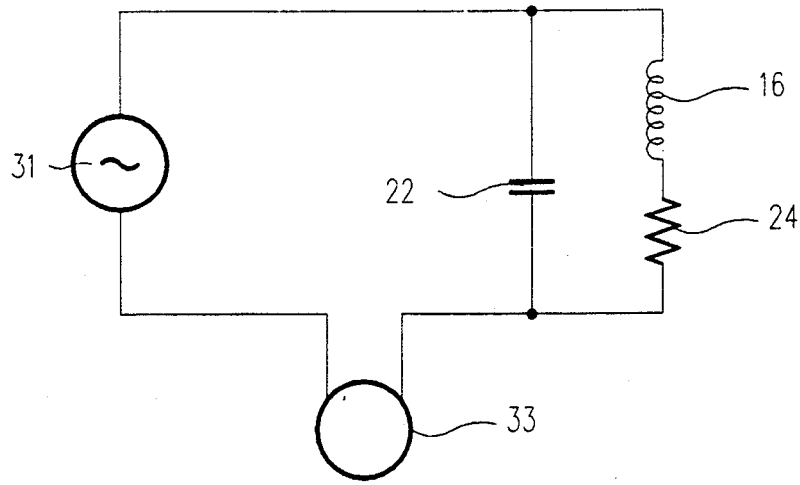
FIG. 4

TANK CIRCUIT SENSOR FOR MONITORING RESIN GRAPHITE COMPOSITE FIBER DENSITIES

BACKGROUND OF THE INVENTION

1. Field of the Invention

The present invention relates to a method and apparatus for monitoring the fiber density of polymeric composite materials during fabrication, and more particularly to a non-invasive method and apparatus that can be used during the fabrication process.

2. Description of the Prior Art

As will be appreciated by those skilled in the art, composite polymeric materials comprise multiple layers of a fiber material, such as a carbon fiber material, impregnated with a polymer, usually a thermosetting polymer. The layers of material and the thermosetting polymer are fabricated into a solid piece by the simultaneous application of heat and pressure. Certain important physical characteristics of the fabricated piece, such as its sheer strength, are a function if its fiber density.

There have been proposals in the prior art relating to monitoring a thermosetting polymer composite during the fabrication process. U.S. Pat. No. 4,891,591 to Johnston et al., discloses a nonintrusive method of monitoring the cure (i.e., extent of reaction) of a polymeric material using an electromagnetic field to sense a change of resistance of the polymeric material in the electromagnetic field that occurs during curing. This change of resistance is used to vary the impedance of an alternating voltage power supply that produces the electromagnetic field and which change of impedance is measured periodically or continuously to monitor the cure of said polymeric material. Apparatus for practicing the method of that invention may include a nonintrusive sensing head providing an inner, electromagnetic core within an open ended outer pot formed of magnet material, the open end of the pot core being positioned from a selected area of the surface of a sheet of the polymeric material. An alternating voltage supply circuit that includes an inductance coil around said electromagnetic core and a capacitor connected in parallel with said inductance coil to form a resonant tank circuit when energized. The resulting change in resistance of the polymeric material opposite the open end (a function of the curing of the material), is measured as a corresponding change in the impedance of said power supply circuit to thereby monitor the curing of the polymeric material in the selected area.

SUMMARY OF THE INVENTION

An object of this invention is the provision of an improved method and apparatus of monitoring the fiber density of fabricated polymeric composite materials; a non-invasive method and apparatus that can be used to control the fabricated process.

Briefly, this invention contemplates the provision of an L-C circuit (tank circuit) located in close proximity to the polymer impregnated composite material layers during the fabrication process. Applicant has determined that the resonant frequency of the tank circuit and the shape of the frequency absorption curve vary as a function of the fiber density of the polymer impregnated composite material. The frequency of the input to the tank circuit is periodically swept through a range of frequencies, and the tank circuit impedance measured to determine the resonant frequency of the L-C tank circuit and shape of the frequency absorption curve. Data relating fiber density to tank circuit resonant frequency and frequency spread may be determined empirically for a particular combination of polymer and fiber materials. In operation, the relational data is used to convert frequency spread and resonant frequency data to fiber density or percent fiber data. Advantageously, the relational data can be stored in a computer memory and fiber density information can be provided continuously to control the process.

BRIEF DESCRIPTION OF THE DRAWINGS

The foregoing objects, aspects and advantages will be better understood from the following detailed description of a preferred embodiment of the invention with reference to the drawings, in which:

FIG. 1 is an overall block diagram of one embodiment of a system in accordance with the teachings of this invention FIG. 2 is a sectional view of one embodiment of a sensing in accordance with this invention.

FIG. 3 is a top view of the coil shown in FIG. 2.

FIG. 4 is a schematic of an L-C tank circuit.

DETAILED DESCRIPTION OF A PREFERRED EMBODIMENT OF THE INVENTION

Figure 5:
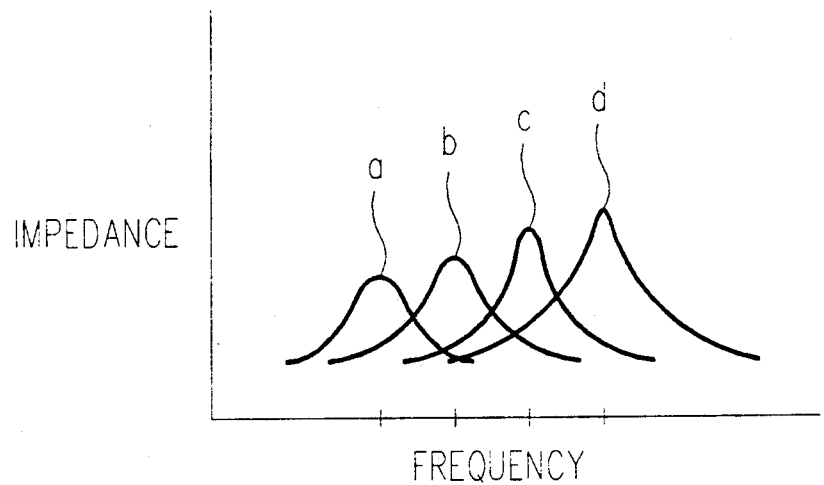
FIG. 5 is a graph illustrating the relation between impedance of the tank circuit and fiber density of the composite.

Referring now to FIG. 1, one embodiment of a system for monitoring the fiber density of a composite material employs a sensor 10 located inside a pressure autoclave 12 adjacent to one surface of a stack of fiber material sheets 14 impregnated with a polymer. In a typical application, the fiber material sheets are formed of loosely woven carbon filaments soaked in a thermosetting polymer such as an epoxy or polyimide. During the course of fabrication, the percentage of fibrous material typically increases from an initial percentage in the range of 30% to 40% to a final percentage in the range of 55% to 65%. At the start of the molding process, a typical stack is on the order of ½-inch thick and is typically compacted to a thickness on the order of 50% percent of the original thickness.

The sensor 10 is shown in greater detail in FIGS. 2, 3 and 4. It comprises an inductive coil 16 wound on the central post 18 of a ferrite pot 20. The sensor includes a capacitive reactance (capacitor 22 in FIG. 4) to form in combination with the coil a R-C tank circuit whose resonant frequency is in a convenient range. In some cases the parasitic capacitance of the circuit is sufficient, and in other cases a discrete capacitor is used.

Figure 6:
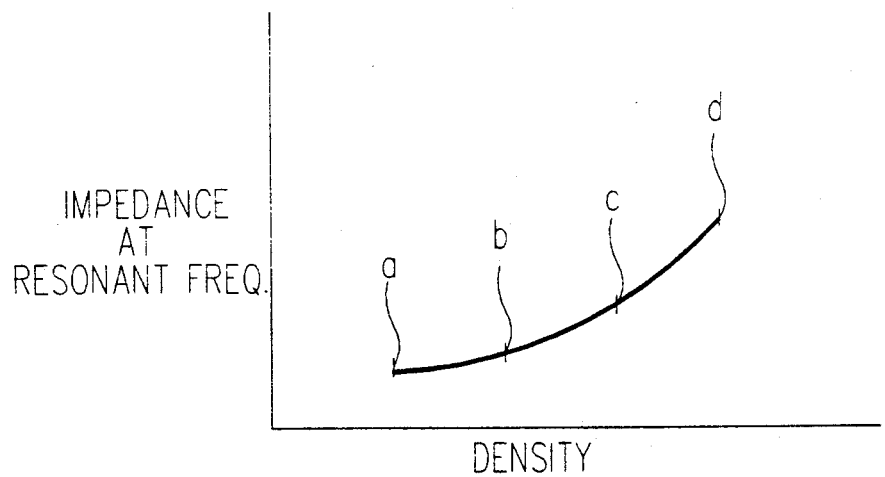
FIG. 6 is a graph illustrating the relation between fiber density and resonant frequency/frequency spread.

The field produced by the coil 16 bulges slightly into the region above the end of the post 18 so that the effective resistance in series with the coil (resistor 24 in FIG. 4) is a function in part of the permeability of the region adjacent the end of the coil. Applicant has established that the permeability of the soaked stack of fibrous material changes as the fiber density of the stack increases. In addition, the capacitive and inductive reactance of the L-C circuit changes with a change in fiber density of the material. Thus, as the fiber density of the stack increases, the resonant frequency of the L-C tank circuit changes and the effective resistance 24 in series with the inductor overall impedance of circuit at the resonant frequency changes. This effect for a particular fiber is illustrated in FIG. 5, which shows a characteristic spreading of the frequency absorption curve and a shift in resonant frequency for stack densities a, b, c and d. For a given woven fiber material and thermosetting polymer, the densities at points such as a, b, c and d can be determined empirically and used to relate impedance at resonance frequency to fiber density, as shown in FIG. 6. Here it should be noted that applicant has established that there is a single value relation between circuit impedance at resonant frequency and fiber density.

Referring now back to FIGS. 1 and 4, an LF impedance analyzer 30 can be used to sweep tank circuit detector 10 through a range of signal frequencies (a range broad enough to include the resonant frequency of the circuit throughout the fabrication process) and simultaneously measure the overall impedance of the tank circuit. In the schematic diagram of FIG. 4 these components are illustrated separately as a variable frequency signal generator 51 and an a.c. impedance meter 53.

In this embodiment of the invention, the analogue output of the LP impedance analyzer 30 is coupled to an analogue to digital convertor 32. The digitized output of the convertor 32 is coupled to a suitable microprocessor 34 where the maximum value for each frequency sweep (peak detection routine 36) is detected and coupled to a look-up table 38 where it is used to address a stored value of fiber density or percentage of fiber corresponding to the measured impedance of the tank circuit at resonance. The stored value can be printed on a printer or recorder 40 and/or used to control the inputs to the pressure autoclave.

While the invention has been described in terms of a single preferred embodiment, those skilled in the art will recognize that the invention can be practiced with modification within the spirit and scope of the appended claims.

Having thus described our invention, what we claim as new and desire to secure by Letters Patent is as follows:

1. In a process for fabricating a multi-layer stack of impregnated fiber material by the application of heat and pressure to the stack in an enclosure, a method for monitoring the fiber density of the material during the molding process, comprising the steps:

placing a tank circuit inductor in said enclosure in close proximity to one surface of said stack of fiber material;

storing values which correlate tank circuit impedance at tank circuit resonance with the fiber density of said stack of impregnated fiber material;

during said molding process, repeatedly sweeping an input signal to said tank circuit through a range of frequencies that includes the resonant frequency of said tank circuit;

detecting the impedance of said tank circuit at said resonant frequency; and determining the fiber density of said fiber material during said molding process from said stored values.

* * * * *

UNITED STATES PATENT AND TRADEMARK OFFICE
CERTIFICATE OF CORRECTION

PATENT NO. : 5,119,022
DATED : June 2, 1992
INVENTOR(S) : Kranbuehl et al.

It is certified that error appears in the above—identified patent and that said Letters Patent is hereby corrected as shown below:

Column 1, before line 8, please insert:

This invention was made with Government support under contract NAG-1-237 awarded by NASA. The Government has certain rights in this invention.

Signed and Sealed this

Sixteenth Day of March, 1993

Attest:

STEPHEN G. KUNIN

Attesting Officer

Acting Commissioner of Patents and Trademarks